United States Patent [19]

Dagani

[11] 4,246,175

[45] Jan. 20, 1981

[54] SYNTHESIS OF 5-CYANO-1-HYDROCARBYLPYRROLE-2-ACETIC ACID

[75] Inventor: Michael J. Dagani, Baton Rouge, La.

[73] Assignee: Ethyl Corporation, Richmond, Va.

[21] Appl. No.: 43,140

[22] Filed: May 29, 1979

[51] Int. Cl.$^3$ ............................................. C07D 207/34
[52] U.S. Cl. ............................. 260/326.2; 260/326.47
[58] Field of Search ........................ 260/326.2, 326.47

[56] References Cited

U.S. PATENT DOCUMENTS

| | | | |
|---|---|---|---|
| 3,752,826 | 8/1973 | Carson | 260/326.2 |
| 3,755,307 | 8/1973 | Carson | 260/326.2 |
| 3,803,169 | 4/1974 | Carson | 260/326.2 |
| 3,803,171 | 4/1974 | Carson | 260/326.2 |
| 4,048,191 | 9/1977 | Carson | 260/326.2 |

FOREIGN PATENT DOCUMENTS 2014131   8/1979   United Kingdom .

OTHER PUBLICATIONS

Wong et al., The Journal of Pharmacology, vol. 185, pp. 127–138 (1973).
Blinn et al., J. Amer. Chem. Soc. 76, pp. 37–39 (1954).

*Primary Examiner*—Mary C. Lee
*Attorney, Agent, or Firm*—Donald L. Johnson; John F. Sieberth

[57] ABSTRACT

When reacting a 2,2,2-trichloro-1-(N-hydrocarbylpyrryl-2)-ethanol in solution with a cyanating reagent under basic conditions, advantages are achieved by performing the reaction in an aqueous reaction medium containing at least 3 equivalents of calcium hydroxide per mole of the 2,2,2-trichloro-1-(N-hydrocarbylpyrryl-2)-ethanol used in the reaction. Good yields are achieved in short reaction times. Large excesses of cyanating reagents are not required. It is unnecessary to add components to the reaction vessel on a periodic basis in order to achieve good yields. And it is possible to isolate the desired product in the form of a calcium salt by a facile procedure. This enables the desired product to be formed by acidification of the isolated calcium salt without the hazards of toxic HCN generation.

11 Claims, No Drawings

SYNTHESIS OF 5-CYANO-1-HYDROCARBYLPYRROLE-2-ACETIC ACID

INTRODUCTION

This invention relates to an improved method for the synthesis of 5-cyano-1-hydrocarbylpyrrole-2-acetic acid, compounds which are particularly useful as chemical intermediates in the production of 5-acyl-1-hydrocarbylpyrrole-2-acetic acids.

BACKGROUND

A wide variety of 5-acyl-1-hydrocarbylpyrrole-2-acetic acids are known to possess useful pharmacological properties. For example, 1-methyl-5-p-toluoylpyrrole-2-acetic acid has a marked anti-inflammatory activity [J. Pharmacology and Experimental Therapeutics, 185, 127 (1973)]. See also U.S. Pat. Nos. 3,752,826; 3,755,307; 3,803,169; 3,803,171 and 4,048,191 (the disclosures of which are incorporated herein) which describe, inter alia, numerous 5-acyl-1-hydrocarbylpyrrole-2-acetic acids having anti-inflammatory and analgetic activities.

In copending application Ser. No. 963,673, filed Nov. 27, 1978 (the disclosure of which is incorporated herein), Kondo, Suda and Tunemoto describe a novel and useful three-step synthesis for producing 5-acyl-1-hydrocarbylpyrrole-2-acetic acid. In the second step of this process, a novel compound—viz., a 5-cyano-1-hydrocarbylpyrrole-2-acetic acid—is produced by reacting 2,2,2-trichloro-1-(N-hydrocarbylpyrryl-2)-ethanol, also known as 1-hydrocarbyl-(2',2',2'-trichloro-1'-hydroxyethyl)-pyrrole, with a cyanating reagent under basic conditions, preferably in a solvent. Examples of the solvent used for this reaction are alcohols such as methanol and ethanol, ethers such as ether, dioxane, THF, and like polar solvents such as dimethyl formamide, dimethyl sulfoxide, and sulfolane, and their mixed solvent with water. Kondo et al. indicate that in this reaction the best results have been obtained using a mixture of methanol and water as the reaction solvent, that the reaction proceeds at or under room temperature, and that, if necessary, the reaction mixture can be heated.

Examples of the cyanating reagent used in their process include inorganic cyanides such as potassium cyanide, sodium cyanide, cuprous cyanide, and the like, and acetone cyanohydrin and the like. To establish the basic reaction conditions, Kondo et al. prefer that the cyanation be performed in the presence of alkali metal salts such as sodium carbonate, potassium carbonate and the like; alkali metal hydroxides such as sodium hydroxide, potassium hydroxide and the like; or alkali metal alkoxides such as sodium methoxide, sodium ethoxide, potassium methoxide, and the like (in this case, the presence of water is essential). Use of sodium hydroxide or potassium hydroxide is most preferred.

Another way of achieving the basic conditions for the Kondo et al. reaction involves use of a large amount of the cyanating reagent when it itself is a base.

As pointed out in the foregoing application, when the reaction of the 2,2,2-trichloro-1-(N-hydrocarbylpyrryl-2)-ethanol with the cyanating reagent is performed under the above conditions and when the acidic product is separated from the resulting reaction mixture, for example, by extraction with alkali and subsequent acidification, the desired 5-cyano-1-hydrocarbylpyrrole-2-acetic acid can selectively be obtained.

While the foregoing process represents a distinct contribution to the art, it nevertheless does possess several drawbacks. To achieve optimum yields large excesses of cyanating reagents were used, NaOH or KOH was added to the reaction mixture on a periodic basis during the reaction, and long reaction times were employed. For instance, in their Example 6, 2,2,2-trichloro-1-(N-methylpyrryl-2)-ethanol was reacted with sodium cyanide (500% excess) in aqueous methanol at 30°-35° C. while feeding aqueous potassium hydroxide (33% excess) over a 20-hour period. After an additional two hours of reaction, the 5-cyano-1-methylpyrrole-2-acetic acid was obtained in 58 percent yield. Further, to recover the product from the reaction solution, the procedure used involved diluting the reaction mixture with water, washing with methylene chloride, carefully acidifying the aqueous layer with HCl, extracting the acidified layer with methylene chloride, washing the extracts with brine, drying the extracts over magnesium sulfate, concentrating the dried extract, and then subjecting the extract to chromatography on silica gel using a hexane-ethyl acetate eluent. Besides involving a number of operations, such a recovery procedure suffers from the hazards of HCN generation during the acidification step.

THE INVENTION

An improvement in the Kondo et al. procedure for producing 5-cyano-1-hydrocarbylpyrrole-2-acetic acid has now been discovered. This improved process enables the reaction to be carried out with good yields in short reaction periods, oftentimes in two hours or less. In addition, large excesses of the cyanating reagent are not required. In fact, NaCN or KCN, which are preferred cyanating reagents, can be employed in stoichiometric (i.e., equimolar) amount relative to the 2,2,2-trichloro-1-(N-hydrocarbylpyrryl-2)-ethanol. Further, there is no need to periodically add any of the materials used in the reaction mixture—all of the materials can be introduced in any suitable order and manner into the reaction vessel in which the reaction is to be performed. And in the process of this invention, it is possible to isolate the desired product in the form of a calcium salt by a facile procedure. This in turn makes it possible to produce the desired 5-cyano-1-hydrocarbylpyrrole-2-acetic acid by acidification of the isolated calcium salt without encountering the hazards associated with generation of toxic HCN.

In accordance with this invention, the process for preparing 5-cyano-1-hydrocarbylpyrrole-2-acetic acid wherein a 2,2,2-trichloro-1-(N-hydrocarbylpyrryl-2)-ethanol is reacted in solution with a cyanating reagent under basic conditions is improved in that the reaction is performed in an aqueous reaction medium containing at least three equivalents (i.e., at least 1.5 moles) of calcium hydroxide per mole of the 2,2,2-trichloro-1-(N-hydrocarbylpyrryl-2)-ethanol used in the reaction. In other words, the basic (alkaline) conditions under which the reaction is performed are due at least in part to the use of calcium hydroxide in a water-containing reaction medium. Use of cyanating reagents which are themselves alkaline substances (NaCN, KCN, etc.) will also contribute to the basicity of the reaction medium.

The amount of calcium hydroxide present in the aqueous reaction medium is susceptible to considerable variation provided that the medium contains at least about three equivalents per mole of the 2,2,2-trichloro-1-(N-hydrocarbylpyrryl-2)-ethanol used in the reaction. For example, experiments have been successfully performed with 4, 6, and 8 equivalents of calcium hydroxide per mole of 2,2,2-trichloro-1-(N-hydrocarbylpyrryl-2)-ethanol. From a practical standpoint, it is preferred to use from 3 to 5 equivalents of calcium hydroxide, 4 equivalents being particularly desirable. The calcium hydroxide may be introduced into the reaction system in solid or slurry form and, if desired, may be formed in situ by the addition of calcium oxide to the aqueous reaction system.

The aqueous reaction medium may be composed either of water or water admixed with an appropriate organic solvent of the type described by Kondo et al. Preferred aqueous reaction media for use in the present process include mixtures of methanol and water and mixtures of dimethyl sulfoxide and water. While the proportions in such mixtures may be varied, the available experimental evidence indicates that in the case of methanol and water, approximately equal volumes afford the highest yields of the desired product. In addition, equal volumes of dimethyl sulfoxide and water gave a good yield in a short reaction period. Accordingly, the use of these co-solvents in approximately equal volumes constitutes a particularly preferred embodiment of this invention. If desired, phase transfer catalysts such as tetrabutylammonium bromide may be used in the reaction mixtures, although to date no particular advantage has been found for their use.

Cyanating reagents used in the process of this invention include such compounds as acetone cyanohydrin, calcium cyanide, potassium cyanide, sodium cyanide, and the like. As noted above, KCN and NaCN, either alone or in combination, are the preferred cyanating reagents. While variations in proportions are possible, generally the system will contain no more than about 4 equivalents of the cyanating reagent per mole of the 2,2,2-trichloro-1-(N-hydrocarbylpyrryl-2)-ethanol used in the reaction. Although there is some improvement in yield associated with use of higher concentrations of the cyanating reagent, this advantage is offset by the increased costs and waste disposal problems incurred at the higher concentrations. For this reason, it is generally preferred to use from 1 to 2 equivalents of the cyanating reagent (most preferably, about 1.25 to about 1.5 equivalents) per mole of the 2,2,2-trichloro-1-(N-hydrocarbylpyrryl-2)-ethanol used in the reaction. In fact, the reaction performs very well even when using 1 equivalent of NaCN or KCN.

Reaction temperatures may range from room temperature or below up to about 100° C. Since the reaction rate is increased with increasing temperature, it is generally preferred to conduct the reaction at a temperature within the range of about 50° to about 90° C. And, of course, in selecting the reaction temperature, the boiling point of the solvent being used and the pressure under which the reaction is being conducted should be taken into consideration. When using the preferred methanol-water systems, the reaction is desirably conducted at reflux (about 76° C. at atmospheric pressure). Ordinarily, at temperatures of 50° C. and above, reaction times of four hours or less will result in good yields of the desired product and in most cases, use of reaction periods of two hours or less is preferred.

Any of a variety of 2,2,2-trichloro-1-(N-hydrocarbylpyrryl-2)-ethanols can be subjected to the process of this invention. These compounds can be prepared by the method of R. C. Blinn et al. as reported in J. Am. Chem. Soc, 76, 37-39 (1954) or, more preferably, by the process described in the foregoing application of Kondo et al., or most preferably, by the process described in my copending application Ser. No. 28,317, filed Apr. 7, 1979 (the disclosure of which is incorporated herein). Because of its utility for the manufacture of 1-methyl-5-p-toluoylpyrrole-2-acetic acid, a commercially produced anti-inflammatory agent, 2,2,2-trichloro-1-(N-methylpyrryl-2)-ethanol is particularly preferred for use in the process of this invention. However, hydrocarbyl substituents other than methyl may be on the nitrogen atom, and either or both of the 3 and 4 positions of the pyrrole ring may carry innocuous substituents (lower alkyl, etc.). Such substituents would not be expected to significantly affect the efficacy of the present process.

At temperatures of 30° C. and below, the calcium salts of 5-cyano-1-hydrocarbylpyrrole-2-acetic acids have relatively low solubility in a number of aqueous media such as water itself, aqueous methanol, and the like. For example, the solubility of calcium 5-cyano-1-methylpyrrole-2-acetate in water at 30° C. is 2.5 percent by weight. On the other hand, the solubility of this salt in the same solvent at 90° C. is 10.4 percent by weight. Such solubility characteristics render it possible in accordance with this invention to isolate the desired product from the reaction solution in the form of a calcium salt. While there are a number of procedures by which such isolation may be effected, a preferred procedure for use on completion of the reaction involves physically separating excess solid calcium hydroxide from the reaction mixture, concentrating the reaction mixture by vaporizing off a portion of the solvent so as to cause the calcium salt of the 5-cyano-1-hydrocarbylpyrrole-2-acetic acid to form as a solid phase, and then isolating this solid phase.

A particular advantage of such a procedure is that this enables the product to be isolated in relatively pure form and subsequently acidified to the corresponding 5-cyano-1-hydrocarbylpyrrole-2-acetic acid without encountering the hazards associated with generation of toxic HCN. Accordingly, when performing the concentration step, care should be exercised to not over-concentrate the system so that the resultant solid phase occludes or absorbs a significant amount of unreacted cyanating reagent. In this connection, partial concentration of the reaction mixture followed by cooling of the solution to induce crystallization is a desirable technique.

Because of its desirable solubility characteristics in water, calcium 5-cyano-1-methylpyrrole-2-acetate, after isolation as a precipitate from the reaction mixture followed by simple washing with cold water and acetone, and drying, was found to have a purity of about 90 percent. Recrystallization yields an essentially pure product. It is interesting to note that calcium 5-cyano-1-methylpyrrole-2-acetate has about the same water solubility as the corresponding barium salt.

It will, of course, be appreciated that other procedures for the isolation or recovery of the 5-cyano-1-hydrocarbylpyrrole-2-acetic acid product may be used. To illustrate, the cooled reaction mixture may be acidified with a strong mineral acid such as 6N HCl to a pH of about 1 to 2. (Caution should be exercised in this operation as HCN is liberated.) The acidified solution is then extracted with suitable volumes of a low boiling inert solvent such as methylene chloride and the resultant organic solution evaporated to dryness. The product residue, usually in the form of a dark solid, is then dissolved with an appropriate volume of hot water and the mixture filtered or centrifuged to remove the undissolved tars and oils. Sodium chloride is then added to the water solution which is then re-extracted with a low boiling inert solvent (e.g., methylene chloride), and the organic solution dried (e.g., with $CaSO_4$) and evaporated to dryness. At this stage the product normally has a purity of about 85 percent. Recrystallization from water or ethyl acetate produces 96 to 99 percent pure product. 5-Cyano-1-methylpyrrole-2-acetic acid purified in this manner and dried at 60° C. in a vacuum oven has a melting point of 123°–124° C. NMR ($CDCl_3$): 3.70 δ (5H, s, N—$CH_3$ and —$CH_2CO_2H$), 6.10 δ (1H, d, J=4 Hz), 6.70 δ (1H, d, J=4 Hz). The infrared (KBr disc) shows strong nitrile (2230 $cm^{-1}$) and carbonyl (1740 $cm^{-1}$) absorption.

Alternatively, the crude product may be purified by chromatography with silica gel using ether as the eluent. The 5-cyano-1-methylpyrrole-2-acetic acid elutes in the first four fractions and more polar solvents are necessary to elute the by-products.

The practice and various features, advantages, and embodiments of this invention will become still further apparent from the following illustrative examples and the appended claims.

EXAMPLE 1

To N-methylpyrrole (13.21 grams, 163 mmole) in 41 ml methylene chloride containing glacial acetic acid (0.53 gram) was added chloral (25.2 grams, 171 mmole; nitrogen atmosphere) over 5–10 minutes. The reaction mixture was refluxed for one hour and then added in one portion to a mixture of sodium cyanide (12.0 grams, 244 mmole) and calcium hydroxide (24.1 grams, 326 mmole) in 800 ml of 50 percent (by volume) aqueous methanol. The reaction mixture was stirred and heated (oil bath at 90° C.) at reflux for 1.5–2.0 hours, during which time methylene chloride was allowed to distill overhead. The hot reaction mixture was filtered from excess calcium hydroxide and the filtrate was evaporated (rotary evaporator) to about 200 ml. After standing at room temperature, the cyano-acid calcium salt (i.e., calcium 5-cyano-1-methylpyrrole-2-acetate) precipitated, and was collected by filtration. The solids were washed with a little cold water and then acetone, dried at 60° C. in a vacuum oven to give 12.1 grams tan solid, which starts to soften at 150° C.–160° C. NMR analysis with an internal standard in $D_2O$ showed 90% calcium salt or 10.9 grams (29.8 mmole). The yield was 36 percent based on N-methylpyrrole. NMR examination indicated more calcium salt was present in the filtrate. A small amount of cyano-acid (1–3 mmole) was obtained after acidification and extraction of the excess calcium hydroxide.

EXAMPLES 2 THROUGH 38

A series of cyanation-hydrolysis reactions were carried out to determine the effect of stoichiometry, concentration, reaction temperature, reaction time, and solvent on the yield of the cyano-acid. In the first step of these experiments, the N-methylpyrrole-chloral adduct, viz., 2,2,2-trichloro-1-(N-methylpyrryl-2)-ethanol, was prepared in methylene chloride as in Example 1 (93% yield). In the second step, sodium cyanide was used as the cyanating reagent and in each case the calcium hydroxide was added to the system in a single portion at the start of the reaction. The reaction conditions for the second step of each experiment, including stoichiometry, concentration, reaction temperature, reaction time, and solvent are set forth in the Table. The cyanation reaction mixtures were stirred and in the reactions performed at the higher temperatures the methylene chloride solvent from the first step was recovered by distillation. Upon completion of the cyanation-hydrolysis reaction, the cooled reaction mixture was acidified with 6N HCl to pH of 1–2 (Caution: HCN is liberated). The acidified solution was then extracted three times with 400 ml portions of methylene chloride (dried over $CaCO_3$) and evaporated to dryness. Analysis was performed on the product by means of NMR with an internal standard. The yields shown in the Table are combined yields for the two reaction steps [i.e., formation of the 2,2,2-trichloro-1-(N-methylpyrryl-2)-ethanol and its conversion via cyanation-hydrolysis to 5-cyano-1-methylpyrrole-2-acetic acid].

TABLE

SYNTHESIS OF 5-CYANO-1-METHYLPYRROLE-2-ACETIC ACID BY CYANATION-HYDROLYSIS OF N-METHYLPYRROLE/CHLORAL ADDUCT

| Example | N-Methylpyrrole-Chloral Adduct Concentration, Molarity | Equivalents NaCN | Equivalents Ca(OH)$_2$ | Time, Hours | Temperature °C. | Solvent (V/V) | Cyano-Acid Yield, % |
|---|---|---|---|---|---|---|---|
| 2 | 0.16 | 1 | 4 | 48 | 36–42 | MeOH/H$_2$O (33/67) | 26 |
| 3 | 0.29 | 2 | 5 | 19 | 36 | MeOH/H$_2$O (50/50) | 24 |
| 4 | 0.50 | 1.12 | 4.5 | 20 | Reflux | MeOH/H$_2$O (62/38) | 39 |
| 5 | 0.25 | 1.25 | 4 | 3.0 | 55 | MeOH/H$_2$O (50/50) | 20 |
| 6 | 0.17 | 2 | 4 | 3.6 | Reflux | MeOH/H$_2$O (50/50) | 52 |
| 7 | 0.15 | 1.5 | 4 | 4.0 | Reflux | MeOH/H$_2$O (50/50) | 52 |
| 8 | 0.62 | 2 | 4 | 3.7 | Reflux | MeOH/H$_2$O (50/50) | 46 |
| 9 | 0.49 | 1.25 | 4 | 1.5 | Reflux | MeOH/H$_2$O (50/50) | 41 |
| 10 | 0.18 | 1.25 | 4 | 1.5 | Reflux | MeOH/H$_2$O (50/50) | 51 |
| 11 | 0.18 | 1.5 | 4 | 1.5 | Reflux | MeOH/H$_2$O (50/50) | 52 |
| 12 | 0.20 | 2 | 4 | 1.5 | 55 | MeOH/H$_2$O (41/59) | 38 |
| 13 | 0.17 | 4 | 4 | 3.6 | Reflux | MeOH/H$_2$O (50/50) | 57 |
| 14 | 0.17 | 2 | 4 | 3.6 | Reflux | Dioxane/H$_2$O (50/50) | 21 |
| 15 | 0.17 | 2 | 6 | 1.5 | Reflux | MeOH/$_2$O (50/50) | 57 |
| 16 | 0.17 | 2 | 8 | 1.5 | Reflux | MeOH/H$_2$O (50/50) | 56 |
| 17 | 0.17 | 2 | 3 | 1.5 | Reflux | MeOH/H$_2$O (50/50) | 51 |
| 18 | 0.17 | 6 | 4 | 3.7 | Reflux | MeOH/H$_2$O (50/50) | 49 |
| 19 | 0.17 | 2 | 4 | 1.5 | Reflux | MeOH/H$_2$O (75/25) | 20 |
| 20 | 0.17 | 2 | 4 | 1.5 | Reflux | MeOH/H$_2$O (25/75) | 38 |
| 21 | 0.17 | 2 | 4 | 1.5 | Reflux | MeOH/H$_2$O (50/50) | 52 |
| 22 | 0.17 | 2 | 4 | 2.0 | Reflux | THF/H$_2$O (50/50) | <10 |
| 23 | 0.17 | 2 | 4 | 1.5 | Reflux | i-PrOH/H$_2$O (50/50) | 31 |
| 24 | 0.17 | 2 | 4 | 1.5 | Reflux | DMF/H$_2$O (50/50) | 20 |

TABLE-continued
SYNTHESIS OF 5-CYANO-1-METHYLPYRROLE-2-ACETIC ACID BY
CYANATION-HYDROLYSIS OF N-METHYLPYRROLE/CHLORAL ADDUCT

| Example | N-Methylpyrrole-Chloral Adduct Concentration, Molarity | Equivalents NaCN | Equivalents Ca(OH)$_2$ | Time, Hours | Temperature °C. | Solvent (V/V) | Cyano-Acid Yield, % |
|---|---|---|---|---|---|---|---|
| 25 | 0.17 | 2 | 4 | 1.5 | Reflux | DMSO/H$_2$O (50/50) | 47 |
| 26 | 0.17 | 2 | 4 | 1.5 | Reflux | Dioxane/H$_2$O (50/50) | 29 |
| 27 | 0.17 | 2 | 4 | 2.5 | 65 | MeOH/H$_2$O (50/50) | 44 |
| 28 | 0.17 | 2 | 4 | 23.0 | 25 | MeOH/H$_2$O (50/50) | 42 |
| 29 | 0.41 | 2 | 4 | 1.5 | Reflux | MeOH/H$_2$O (50/50) | 46 |
| 30 | 0.63 | 2 | 4 | 1.5 | Reflux | MeOH/$_2$O (50/50) | 41 |
| 31 | 0.082 | 2 | 4 | 1.5 | Reflux | MeOH/H$_2$O (50/50) | 44 |
| 32 | 0.082 | 2 | 4 | 4.0 | Reflux | MeOH/H$_2$O (50/50) | 47 |
| 33 | 0.20 | 2 | 4 | 1.8 | Reflux | MeOH/H$_2$O (50/50) | 34 |
| 34 | 0.25 | 1.5 | 4 | 1.5 | 90 | H$_2$O$^a$ | 33 |
| 35 | 0.25 | 2 | 4 | 1.5 | Reflux | MeOH/H$_2$O (50/50)$^a$ | 50 |
| 36 | 0.18 | 1 | 4 | 1.5 | Reflux | MeOH/H$_2$O (50/50) | 47 |
| 37 | 0.18 | 1.25 | 4 | 1.5 | Reflux | MeOH/H$_2$O (50/50) | 50 |
| 38 | 0.18 | 1.5 | 4 | 1.5 | Reflux | MeOH/H$_2$O (50/50) | 51 |
| Control | 0.18 | 6 | nil | 1.5 | Reflux | MeOH/H$_2$O (50/50) | 25 |
| Control | 0.18 | 6 | nil | 72 | 25 | MeOH/H$_2$O (50/50) | 29 |

$^a$Tetrabutyl ammonium bromide (2 mole percent based on the adduct) added.

EXAMPLE 39

Chloral (4.0 grams, 27.1 mmole) was added to N-methylpyrrole (2.0 grams, 24.7 mmole) in 10 grams of methylene chloride containing 0.1 gram of glacial acetic acid. After refluxing this reaction mixture for one hour, it was added in one portion to a mixture of sodium cyanide (1.85 grams, 37 mmole) and calcium hydroxide (3.65 grams, 49.3 mmole) in 140 ml of 50 percent (by volume) aqueous methanol. The resultant reaction mixture was stirred and heated at reflux for two hours by means of an oil bath. The cooled reaction mixture was acidified with 6N HCl to a pH of about 1 to 2 (Caution: HCN liberation). The acidified solution was extracted three times with methylene chloride and the combined methylene chloride solutions evaporated to dryness giving 3.75 grams of dark solids. This crude 5-cyano-1-methylpyrrole-2-acetic acid was reacted with 32 grams of acetone dimethyl ketal and 32 grams of methanol in the presence of 0.5 gram of p-toluene sulfonic acid under a nitrogen atmosphere for approximately 15 hours at 30° to 35° C. The reaction mixture was diluted with diethyl ether and washed several times with water, and the organic solution was dried over calcium sulfate. Evaporation of the ether solution gave 2.45 grams of the methyl ester of 5-cyano-1-methylpyrrole-2-acetic acid as a dark oil. Analysis by NMR with an internal standard showed the methyl ester to have a purity of about 87.6 percent. It was produced in 49 percent isolated yield.

EXAMPLE 40

To a 500 ml baffled glass reactor fitted with an agitator and a reflux condenser were charged 161.9 grams of methylene chloride, 39.6 grams of N-methylpyrrole, and 1.59 grams of glacial acetic acid. This mixture was agitated and heated to reflux temperature (about 47° C.), and over a five minute period 75.6 grams of chloral was added to the refluxing mixture on a uniform basis. The reaction mixture was refluxed for an additional five minutes. Thereupon, this reaction solution containing the N-methylpyrrole-chloral adduct was cooled to room temperature. Into a 3 liter, agitator-equipped, baffled glass reactor connected to a distillation condenser and a distillation receiver were charged 1200 grams of water, 38.0 grams of sodium cyanide, 951 grams of methanol and 72.3 grams of calcium hydroxide. This agitated mixture was then heated to 50° C. and the above N-methylpyrrole-chloral reaction solution was added over a 25 minute period. As the temperature of the reaction mixture was raised from 50° C. to 78° C., methylene chloride and methanol that distilled out of the reactor (218 grams total) was collected in the distillate receiver. Then, the condenser was rearranged on the apparatus to give total reflux and the reaction was continued at reflux for another two hours. After cooling the reaction product to room temperature, the solids (including calcium hydroxide and tars) were filtered off and the filtrate concentrated to 14 percent of its original weight by vacuum stripping at 20° to 65° C. The concentrate was left overnight in a refrigerator and the resulting crystalline product was filtered off and dried at 65° C. in a vacuum oven. The calcium 5-cyano-1-methylpyrrole-2-acetate was produced in an over-all yield for the two reaction steps of about 52 percent.

Based on the experimental work performed to date, the optimum conditions for performing the process of this invention are deemed to be reaction of 2,2,2-trichloro-1-(N-hydrocarbylpyrryl-2)-ethanol (0.18 M in 50 percent aqueous methanol) with 25 to 50 percent excess sodium cyanide and 33 percent excess calcium hydroxide at reflux at atmospheric pressure for 1.5 hours. The yield in this reaction is about 56 percent based on the 2,2,2-trichloro-1-(N-hydrocarbylpyrryl-2)-ethanol. These conditions result in improved reagent utilizations and shorter reaction times and produce the desired cyano-acid product in about the same yield as the best yield reported by Kondo et al.

Suitable procedures for the conversion of 5-cyano-1-hydrocarbylpyrrole-2-acetic acid to 5-acyl-1-hydrocarbylpyrrole-2-acetic acid are set forth in the Kondo et al. application. An even more desirable procedure is described in copending application Ser. No. 55,039, filed July 5, 1979 (by Edward J. Zaiko).

I claim:
1. In a process for preparing 5-cyano-1-hydrocarbylpyrrole-2-acetic acid by reacting 2,2,2-trichloro-1-(N-hydrocarbylpyrryl)-2)-ethanol in solution with a cyanating reagent under basic conditions, the improvement characterized in that the reaction is performed in an aqueous reaction medium containing at least 3 equivalents of calcium hydroxide per mole of 2,2,2-trichloro-1-(N-hydrocarbylpyrryl-2)-ethanol used in the reaction.

2. A process according to claim 1 wherein the 5-cyano-1-hydrocarbylpyrrole-2-acetic acid is isolated from the reaction solution in the form of a calcium salt.

3. A process according to claim 1 wherein the 5-cyano-1-hydrocarbylpyrrole-2-acetic acid is recovered from the reaction mixture in the form of a calcium salt by physically separating excess solid calcium hydroxide from the reaction mixture, concentrating the reaction mixture by vaporizing off a portion of the solvent so as to cause the calcium salt of the 5-cyano-1-hydrocarbylpyrrole-2-acetic acid to form as a solid phase, and then isolating said solid phase.

4. A process according to claim 1 wherein the cyanating reagent is NaCN or KCN.

5. A process according to claim 1 wherein the aqueous reaction medium is a mixture of methanol and water or dimethyl sulfoxide and water.

6. A process according to claim 1 wherein the aqueous reaction medium is a mixture of methanol and water, and the reaction is performed at reflux.

7. A process according to claim 1 wherein the cyanating reagent is NaCN or KCN and wherein the 2,2,2-trichloro-1-(N-hydrocarbylpyrryl-2)-ethanol is 2,2,2-trichloro-1-(N-methylpyrryl-2)-ethanol.

8. A process according to claim 1 wherein the cyanating reagent is NaCN or KCN employed in an amount of from about 1 to about 2 equivalents per mole of 2,2,2-trichloro-1-(N-hydrocarbylpyrryl-2)-ethanol used in the reaction, wherein the solvent is a mixture of approximately equal volumes of methanol and water, and wherein the reaction is performed at reflux for up to about four hours.

9. A process according to claim 1 wherein the cyanating reagent is NaCN or KCN employed in an amount of from about 1 to about 2 equivalents per mole of 2,2,2-trichloro-1-(N-hydrocarbylpyrryl-2)-ethanol used in the reaction, wherein the aqueous reaction medium contains from 3 to 5 equivalents of calcium hydroxide per mole of 2,2,2-trichloro-1-(N-hydrocarbylpyrryl-2)-ethanol used in the reaction and wherein the reaction is performed at reflux for up to about four hours.

10. A process according to claim 1 wherein the 2,2,2-trichloro-1-(N-hydrocarbylpyrryl-2)-ethanol is 2,2,2-trichloro-1-(N-methylpyrryl-2)-ethanol, wherein the cyanating reagent consists essentially of sodium cyanide employed in an amount of from 1 to 2 equivalents per mole of the 2,2,2-trichloro-1-(N-methylpyrryl-2)-ethanol used in the reaction, wherein the reaction medium is a mixture of approximately equal volumes of methanol and water, wherein the aqueous reaction medium contains from 3 to 5 equivalents of calcium hydroxide per mole of the 2,2,2-trichloro-1-(N-methylpyrryl-2)-ethanol used in the reaction, and wherein the reaction is performed at reflux for up to about four hours.

11. Calcium 5-cyano-1-methylpyrrole-2-acetate.

* * * * *